(12) United States Patent
Jeon et al.

(10) Patent No.: US 10,354,674 B2
(45) Date of Patent: Jul. 16, 2019

(54) WHITE NOISE GENERATING APPARATUS FOR STRESS RELAXATION AND CONCENTRATION IMPROVEMENT, AND WHITE NOISE GENERATING METHOD USING SAME

(71) Applicants: GAONDIRECTOR CO., LTD., Seoul (KR); Woo Sung Jeon, Anyang-si (KR); Min Cheol Whang, Goyang-si (KR)

(72) Inventors: Woo Sung Jeon, Anyang-si (KR); Min Cheol Whang, Goyang-si (KR); Jung Nylin Lee, Incheon-si (KR)

(73) Assignees: GAONDIRECTOR CO., LTD., Seoul (KR); Woo Sung Jeon, Anyang-si (KR); Min Cheol Whang, Goyang-shi (JP)

( * ) Notice: Subject to any disclaimer, the term of this patent is extended or adjusted under 35 U.S.C. 154(b) by 0 days.

(21) Appl. No.: 15/323,348

(22) PCT Filed: Jun. 19, 2015

(86) PCT No.: PCT/KR2015/006226
§ 371 (c)(1),
(2) Date: Dec. 30, 2016

(87) PCT Pub. No.: WO2016/003096
PCT Pub. Date: Jan. 7, 2016

(65) Prior Publication Data
US 2017/0133035 A1 May 11, 2017

(30) Foreign Application Priority Data
Jul. 2, 2014 (KR) .................. 10-2014-0082513

(51) Int. Cl.
*G10L 21/0324* (2013.01)
*H04R 1/10* (2006.01)
(Continued)

(52) U.S. Cl.
CPC ......... *G10L 21/0324* (2013.01); *A61M 21/02* (2013.01); *G10L 25/63* (2013.01);
(Continued)

(58) Field of Classification Search
CPC .... G10L 21/0324; G10L 25/63; A61M 21/02; A61M 2230/50; A61M 2230/08;
(Continued)

(56) References Cited

U.S. PATENT DOCUMENTS

2003/0078505 A1* 4/2003 Kim .................. A61B 5/0008
600/485
2006/0167576 A1* 7/2006 Rosenberg ........ G06F 17/30032
700/94
(Continued)

FOREIGN PATENT DOCUMENTS

JP 2007000366 A * 1/2007
JP 4630136 B2 * 2/2011
(Continued)

*Primary Examiner* — Bharatkumar S Shah
(74) *Attorney, Agent, or Firm* — Sughrue Mion, PLLC

(57) ABSTRACT

A white noise generating apparatus for stress relaxation and concentration improvement includes: a headset including a microphone for outputting the voice to a communication line, a sound outputting unit for outputting the voice inputted from the communication line, and a sensing unit which is capable of sensing at least one of a pulse wave, a skin current, a skin temperature, and a white noise generator including a stress calculating unit for calculating a stress index from the voice outputted from the microphone, a white noise generating unit for generating white noise and outputting same to the sound output unit, and a control unit for
(Continued)

controlling the white noise generating unit to output white noise sound in accordance with the stress index calculated from the stress calculating unit so that the stress level may be normal.

4 Claims, 4 Drawing Sheets

(51) Int. Cl.
   *H04R 3/00* (2006.01)
   *A61M 21/02* (2006.01)
   *G10L 25/63* (2013.01)
   *H04M 9/08* (2006.01)
   *A61M 21/00* (2006.01)

(52) U.S. Cl.
   CPC .............. *H04M 9/082* (2013.01); *H04R 1/10* (2013.01); *H04R 3/00* (2013.01); *A61M 2021/0027* (2013.01); *A61M 2210/0662* (2013.01); *A61M 2230/005* (2013.01); *A61M 2230/04* (2013.01); *A61M 2230/08* (2013.01); *A61M 2230/50* (2013.01)

(58) Field of Classification Search
   CPC ........ A61M 2230/005; A61M 2230/04; A61M 2021/0027; A61M 2210/0662
   USPC ....................................................... 704/200.1
   See application file for complete search history.

(56) References Cited

U.S. PATENT DOCUMENTS

2011/0185499 A1* 8/2011 Richards .............. G10K 11/175
   5/425
2012/0329432 A1* 12/2012 Gupta .................... G06Q 30/02
   455/414.1

FOREIGN PATENT DOCUMENTS

| KR | 10-081277 B1 | 3/2008 |
| KR | 10-2011-0073404 A | 6/2011 |
| KR | 1020120131253 | * 12/2015 |

* cited by examiner

WHITE NOISE GENERATING APPARATUS FOR STRESS RELAXATION AND CONCENTRATION IMPROVEMENT, AND WHITE NOISE GENERATING METHOD USING SAME

CROSS REFERENCE TO RELATED APPLICATIONS

This application is a National Stage of International Application No. PCT/KR2015/006226 filed Jun. 19, 2015, claiming priority from Korean Patent Application No. 10-2014-0082513, filed on Jul. 2, 2014, the disclosure of which are incorporated herein in their entireties by reference.

FIELD OF THE INVENTION

The present invention relates to a white noise generating headset and method, and more specifically, to a white noise generating headset for stress relaxation and concentration improvement and a white noise generating method using the same which measure a voice, a pulse wave, a skin current, and a skin temperature using a headset used in a telephone conversion or study and then generate white noise capable of relieving stress or improving concentration to an ear set part of the headset.

BACKGROUND OF THE INVENTION

Generally, a hearing function of a person is one of the most organ developed for the first time in sensory organs, and if hearing stimuli are appropriately applied to the human body, stimuli for the left brain and the right brain are accelerated to give many influences to the development of the brain and other senses such as smell and vision.

According to the researches using sounds, natural sounds contain many high-frequency sounds, and when a person hears the natural sounds, accordingly, he or she feels relaxation and generates alpha waves from his or her brain. Moreover, music is to improve a communication capability of people in the social activities and give an influence to the cognitive function of people.

Most people think noise is an element of inhibiting their work needing cognition performance ability. Conventional technologies related to white noise among various noise are disclosed in Korean Patent Application Publication No. 10-2010-00046 (entitled 'hard disk type language learning device for concentration reinforcement'), Korean Patent Application Registration No. 10-0812770 (entitled 'method and apparatus for providing double speed narration voice signal using white noise', and in Korean Patent Application Publication No. 10-2011-0073404 (entitled 'lighting device system having noise control/sound therapy function) and so forth.

The conventional technologies generate white noise to remove noise components by generating white noise or remove noise components, so that a user's concentration is improved, however, they are technologies to generate the white noise. Accordingly, they do not use the white noise to improve the concentration in work or study through the stress relaxation or the maintenance of appropriate tension by using white noise.

SUMMARY OF THE INVENTION

Accordingly, the present invention has been made to solve the above-mentioned problems in the prior art, and an object of the present invention is to provide a white noise generating apparatus for stress relaxation and concentration improvement and a white noise generating method using the same which measure a voice, a pulse wave, and a skin current using a headset used in a telephone conversion or study and then generate white noise capable of relieving stress or improving concentration to an ear set part of the headset.

To accomplish the above-mentioned object, according to a first aspect of the present invention, a white noise generating apparatus for stress relaxation and concentration improvement, includes: a headset having a microphone for outputting voice to a communication line, a sound outputting unit for outputting the voice inputted from the communication line, and a sensing unit for sensing at least any one or more of a pulse wave, and a skin current of a wearer thereof; and a white noise generator for calculating a stress index from the voice outputted from the microphone to output white noise sound so that the stress index is within a normal range, the white noise generator including an on/off unit for turning on/off the supply of operating power of the white noise generator, a voice stress calculating unit for calculating the stress index from the voice outputted from the microphone of the headset, a sensing value calculating unit for calculating sensed values including at least any one or more of a pulse wave, and a skin current sensors, a white noise generating unit for generating and outputting the white noise sound to the sound outputting unit of the headset, a memory unit for storing white noise data adequate to normalize stress in accordance with the stress index, the intensity of white noise voice output generated in accordance with the stress index, or the intensity of white noise voice output according to at least one or more physiological signal variations of the pulse wave, and the skin current of the wearer, a control unit for controlling to output the white noise sound in the white noise generating unit to allow the stress to be within a normal range in accordance with the stress index calculated from the voice stress calculating unit and the sensed value calculating unit, and an automatic/manual adjusting unit for automatically or manually performing the control of the white noise sound output by means of the control unit, when a voice is detected from the microphone 11 of the headset 10 and one or more of the pulse wave, and skin current are sensed by the sensors, the voice stress calculating unit 22 calculates a stress index from the detected voice and the sensed value, after the control unit 27 determines whether the stress index is abnormal, if the stress index is abnormal, generating and outputting the white noise from the white noise generating unit 23 to the sound outputting unit 12 of the headset 10 by the control unit 27 so that the stress index is normal is carried out.

According to the present invention, desirably, the memory unit is connected to the control unit.

According to the present invention, desirably, the voice stress calculating unit extracts the voice to express the emotional state through the analysis of the voice, performs the analysis of the extracted voice, compares the analyzed voice with set voice information including a waveform, period and amplitude according to a voice frequency, and calculates the voice stress according to a set table.

To accomplish the above-mentioned object according to a second aspect of the present invention, a white noise generating method for stress relaxation and concentration improvement using a white noise generating apparatus, the white noise generating apparatus includes: a headset having a microphone for outputting voice to a communication line, a sound outputting unit for outputting the voice inputted from the communication line, and a sensing unit for sensing at least any one or more of a pulse wave, and a skin current of a wearer thereof; and a white noise generator including a voice stress calculating unit for calculating a stress index from the voice outputted from the microphone of the headset, a sensing value calculating unit for calculating sensed values including at least any one or more of a pulse wave, and a skin current by the sensing unit, a white noise generating unit for generating and outputting the white noise sound to the sound outputting unit of the headset, a memory unit for storing white noise data adequate to normalize stress in accordance with the stress index, the intensity of white noise voice output generated according to the stress index, or the intensity of white noise voice output in accordance with at least one or more physiological signal variations of the pulse wave, and the skin current of the wearer, a control unit for controlling to output the white noise sound in the white noise generating unit to allow the stress to be within a normal range in accordance with the stress index calculated from the voice stress calculating unit and the sensed value calculating unit for calculating sensed values including at least any one or more of a pulse wave, and a skin current by the sensing unit, and an automatic/manual adjusting unit for automatically or manually performing the control of the white noise sound output by means of the control unit, the white noise generating method including the steps of: detecting the voice outputted from the microphone of the headset and sensing at least one or more of the pulse wave, and skin current of the wearer who wears the headset; calculating by the control unit 27 the stress index from the detected voice and the sensed value; determining whether the stress index calculated is abnormal or not; if the stress index is abnormal, generating and outputting the white noise from the white noise generating unit to the sound outputting unit of the headset again so that the stress index is normal; determining whether the stress index is abnormal or not; if the stress index is still abnormal, determining whether automatic control is set or not; if the automatic control is set, controlling and outputting the white noise sound so that the stress index is within a set value; if the automatic control is not set, determining whether manual control is inputted or not; and if the manual control is inputted, outputting the white noise sound according to the manual control.

According to the present invention, desirably, the white noise generating method further includes the steps of: after the step of controlling and outputting the white noise sound so that the stress index is within the set value or the step of outputting the white noise sound according to the manual control, determining whether the stress index is normal or not again; and if it is determined whether the stress index is normal, maintaining the current output and storing the intensity of the white noise sound output corresponding to the current stress index in the memory unit.

According to the present invention, the white noise generating apparatus and method for stress relaxation and concentration improvement have the following advantages.

Firstly, the voice, pulse wave, and skin current of the wearer who wears a headset and speaks over the telephone are sensed during his or her telephone conversation to calculate the stress index, and using the stress index, the white noise capable of relieving his or her stress or applying an appropriate tension to him or her is generated and outputted to his or her hearing input portions, thereby improving his or her working efficiency.

Secondly, the voice, pulse wave, and skin current of the wearer who wears a headset and studies are sensed during his or her study to calculate the stress index, and using the stress index, the white noise capable of relieving his or her stress or applying an appropriate tension to him or her is generated and outputted to his or her hearing input portions, thereby improving his or her study efficiency.

Thirdly, after the voice, pulse wave, and skin current of the wearer who wears a headset and studies are sensed during his or her telephone conversation or study to calculate the stress index, the white noise is outputted to relieve his or her stress or apply an appropriate tension to him or her, and at this time, the white noise output is automatically controlled so that while he or she does not recognize the white noise during the telephone conversation or study, his or her stress is naturally relieved or his or her appropriate tension is maintained.

Lastly, the levels of the stress relaxation and tension maintaining of the wearer are stored to the form of data, and if necessary, advantageously, they can be relaxed their stress individually and maintained tension optimally.

BRIEF DESCRIPTION OF THE DRAWINGS

The above and other aspects, features and advantages of certain exemplary embodiments of the present invention will be more apparent from the following detailed description taken in conjunction with the accompanying drawings, in which.

EXPLANATIONS ON REFERENCE NUMERALS IN THE DRAWING

Figure 1:
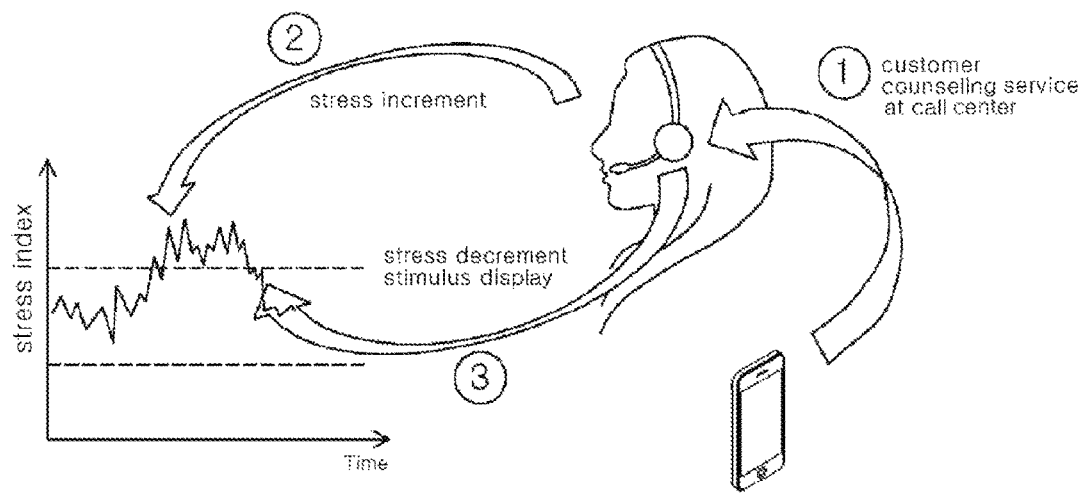
FIG. 1 is a concept view showing a white noise generating headset for stress relaxation and concentration improvement according to the present invention.

10: headset
11: microphone
12: sound outputting unit
13: sensing unit
20: white noise generator
21: on/off unit
22: voice stress calculating unit
23: white noise generating unit
24: memory unit
25: automatic/manual adjusting unit
26: sensed value calculating unit
27: control unit
30: communication line

DETAILED DESCRIPTION OF THE INVENTION

Hereinafter, a preferred embodiment of the present invention will be in detail explained with reference to the attached drawings. All terms used herein, including technical or scientific terms, unless otherwise defined, have the same meanings which are typically understood by those having ordinary skill in the art. The terms, such as ones defined in common dictionaries, should be interpreted as having the same meanings as terms in the context of pertinent technology, and should not be interpreted as having ideal or excessively formal meanings unless clearly defined in the specification. In the description, if it is determined that the detailed explanation on the well known technology related to the present invention makes the scope of the present invention not clear, the explanation will be avoided for the brevity of the description.

Figure 2:
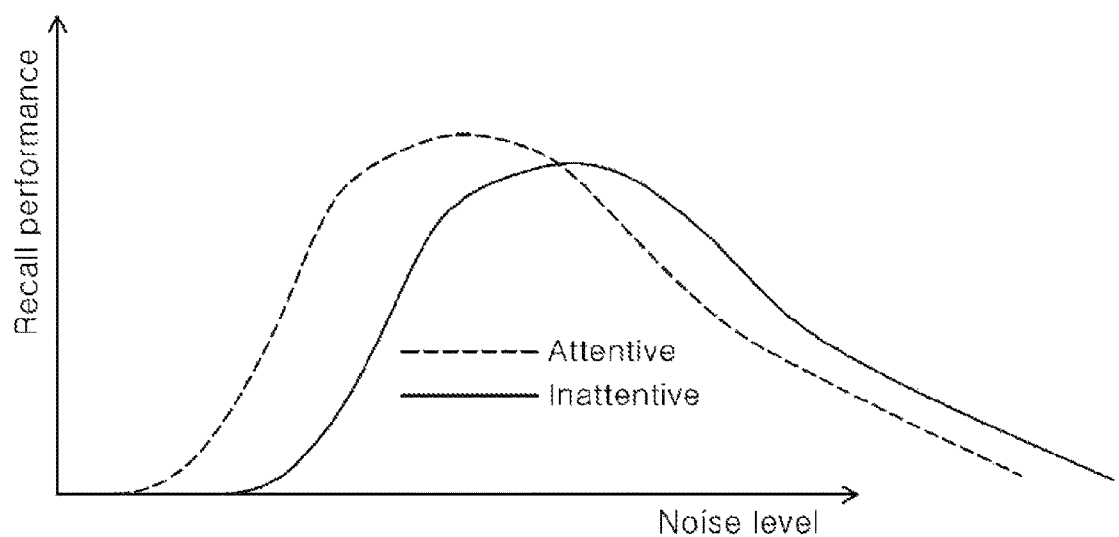
FIG. 2 is a graph showing individual differences of SR (Stochastic Resonance) curves so as to explain stress relaxation and concentration improvement according to the present invention.

FIG. 1 is a concept view showing a white noise generating headset for stress relaxation and concentration improvement according to the present invention, and FIG. 2 is a graph showing individual differences of SR (Stochastic Resonance) curves so as to explain stress relaxation and concentration improvement according to the present invention.

According to the present invention, for example, a white noise generating apparatus (headset) for stress relaxation and concentration improvement is described with illustration while a counselor working at a call center communicates with customer by using telephone. As shown in FIG. 1, because the counselor is under general stress while conducting a telephone conversation with a customer or under direct stress by the conversation with the customer, and such stress has been recently emerged as one of serious social problems. According to the present invention, the white noise generating apparatus for stress relaxation and concentration improvement is provided to generate white noise when his or her stress is increased so that stimuli are applied to a wearer who is a counselor through a sound outputting unit (earphones), thereby reducing his or her stress.

On the other hand, an appropriate amount of white noise helps people's stress relieved or reduced as well as strained properly by maintaining appropriate tension to improve the concentration in their work or study, and FIG. 2 is a graph showing individual differences of SR curves.

In FIG. 2, that is, the performance of recognition test (axis y) shows that two optimal, that is, too high or low noise levels are attenuated with respect to an appropriate noise level (axis x). It can be appreciated that so as to obtain optimal performance, children who are careless or have low performance need much more noise than children who have high concentration and performance. Accordingly, it is understood that both of the children who have high concentration and performance and the children who are careless or have low performance need an appropriate noise level.

Figure 3:
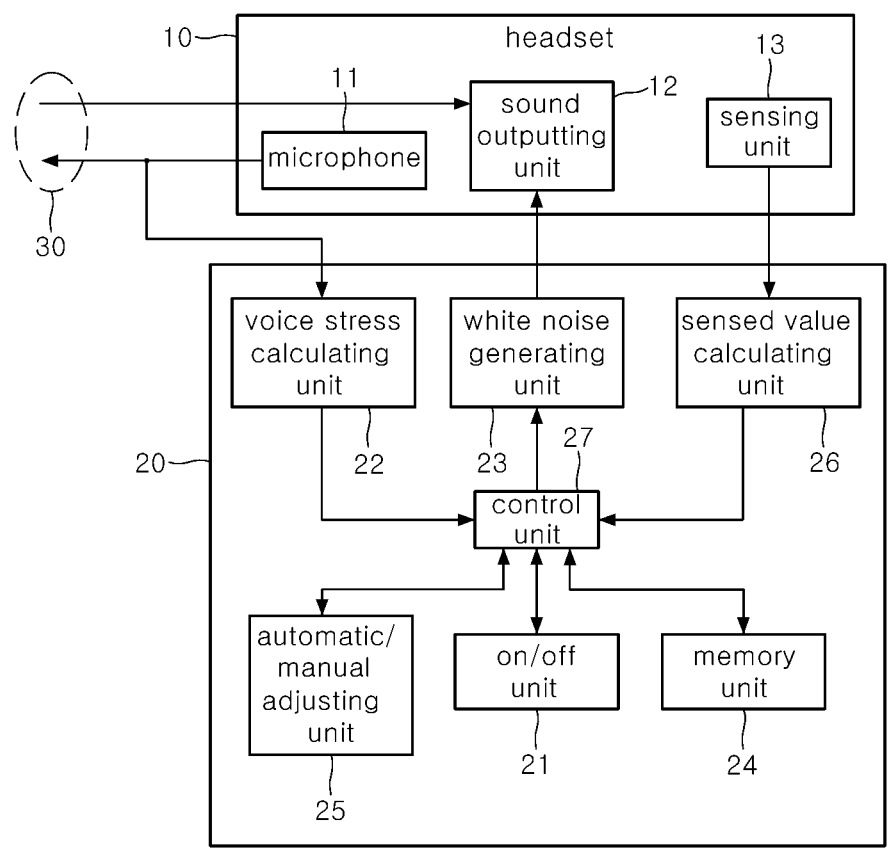
FIG. 3 is a block diagram showing the white noise generating headset for stress relaxation and concentration improvement according to the present invention.

FIG. 3 is a block diagram showing the white noise generating headset including headset for stress relaxation and concentration improvement according to the present invention.

As shown in FIG. 3, the white noise generating apparatus for stress relaxation and concentration improvement according to the present invention largely includes a headset 10 and a white noise generator 20.

In this case, the headset 10 includes a microphone 11 for receiving a wearer's voice while he or she conducts a telephone conversation or studies to output the received voice to a communication line 30, a sound outputting unit 12 for outputting the voice inputted from the communication line 30 to allow the wearer to listen to the voice, and a sensing unit 13 for sensing at least any one or more of a pulse wave, a skin current, and a skin temperature of the wearer.

In this case, the sensing unit 13 may be a PPG (Photoplethsmography) sensor for sensing a pulse wave signal among the bio-medical signals of a human body. At this time, The pulse wave signal measures the bloodstream of the skin, and in this case, light is irradiated to the skin through an LED (Light Emitting Diode) to vary vibration of pulses. At this time, the amount of light reflected to a photodiode is measured. Generally, to measure the PPG, the pulse wave signal is measured from a finger or ear, and of course, it may be measured from the nasal septum, forehead, esophagus and so forth. However, efficient places for the measurement are the ear and finger. However, because impacts or low body temperatures may reduce the bloodstream, they should be considered upon the signal measurement.

Further, the sensing unit 13 may be a GSR (Galvanic Skin Response) sensor for sensing the skin current among the bio-medical signals of the human body. It is found by Fere (in 1888) that when stimuli are applied to a human body, a resistance to a small amount of electric current flowing to the body between two points of the skin is reduced. In this case, the sensor measures the change in the resistance values of the internal tissues of the skin generated by the activities of sweat glands in accordance with the antagonism of sympathetic and parasympathetic nerves. The GSR shows a subtle difference in dynamic activities and emotional excitement relationship, which is used as one component of a lie detector, and in this case, the GSR is used to measure the emotionally excited state.

On the other hand, the sensing unit 13 may be a sensor for sensing SKT (skin temperature) of the human body. In this case, the SKT means the skin temperature of the human body, and when the sympathetic nerves are activated, generally, the skin temperature lowers by contradiction of the blood vessels. When the parasympathetic nerves are activated, contrarily, the skin temperature raises by relaxation of the blood vessels.

Like this, the sensing unit 13 is formed of one or more sensors for measuring the pulse wave, skin current and skin temperature, and it is disposed desirably on the headset 10, more desirably on the ear portions of headphones.

Further, as shown in FIG. 3, the white noise generator 20 includes: an on/off unit 21 for turning on/off the white noise generator 20; a voice stress calculating unit 22 for calculating a stress index from the voice outputted from the microphone 11 of the headset 10; a white noise generating unit 23 for generating and outputting the white noise to the sound outputting unit 12; a memory unit 24 for storing white noise data adequate to normalize stress in accordance with the stress index, the intensity of white noise voice output generated in accordance with the stress index of the wearer, or the intensity of white noise voice output according to the changes of the pulse wave, the skin current and the skin temperature (the wearer's physiological signal variations); an automatic/manual adjusting unit 25 for allowing the wearer to select automatic or manual control for the white noise generator 20; a sensed value calculating unit 26 for calculating a sensed value from one or more of the pulse wave, skin current and skin temperature sensed by the sensing unit 13 of the headset 10; and a control unit 27 for performing operations according to the inputs of the on/off unit 21 and the automatic/manual adjusting unit 25 and controlling the white noise generating unit 23 to generate white noise sound so as to normalize the stress of a wearer with reference to the memory unit 24 in accordance with the stress index and the physiological signal variations calculated from the voice stress calculating unit 22 and the sensed value calculating unit 26.

In this case, the on/off unit 21 and the automatic/manual adjusting unit 25 may be selectively comprised, and the memory unit 24 may be connected to the control unit 27.

Moreover, the voice stress calculating unit 22 extracts the voice through the analysis of the voice, performs the analysis of the extracted voice, compares the analyzed voice with a pre-set voice information, for example, a waveform, period and amplitude according to a voice frequency, and calculates the voice stress. In this case, the analysis of voice is carried out by a common voice analyzer, and the analyzed voice is compared with the stress index made in the form of a table, thereby calculating the voice stress.

On the other hand, normalization of stress includes stress relaxation or reduction as well as the maintenance of appropriate tension to improve the concentration in work or study.

Figure 4:
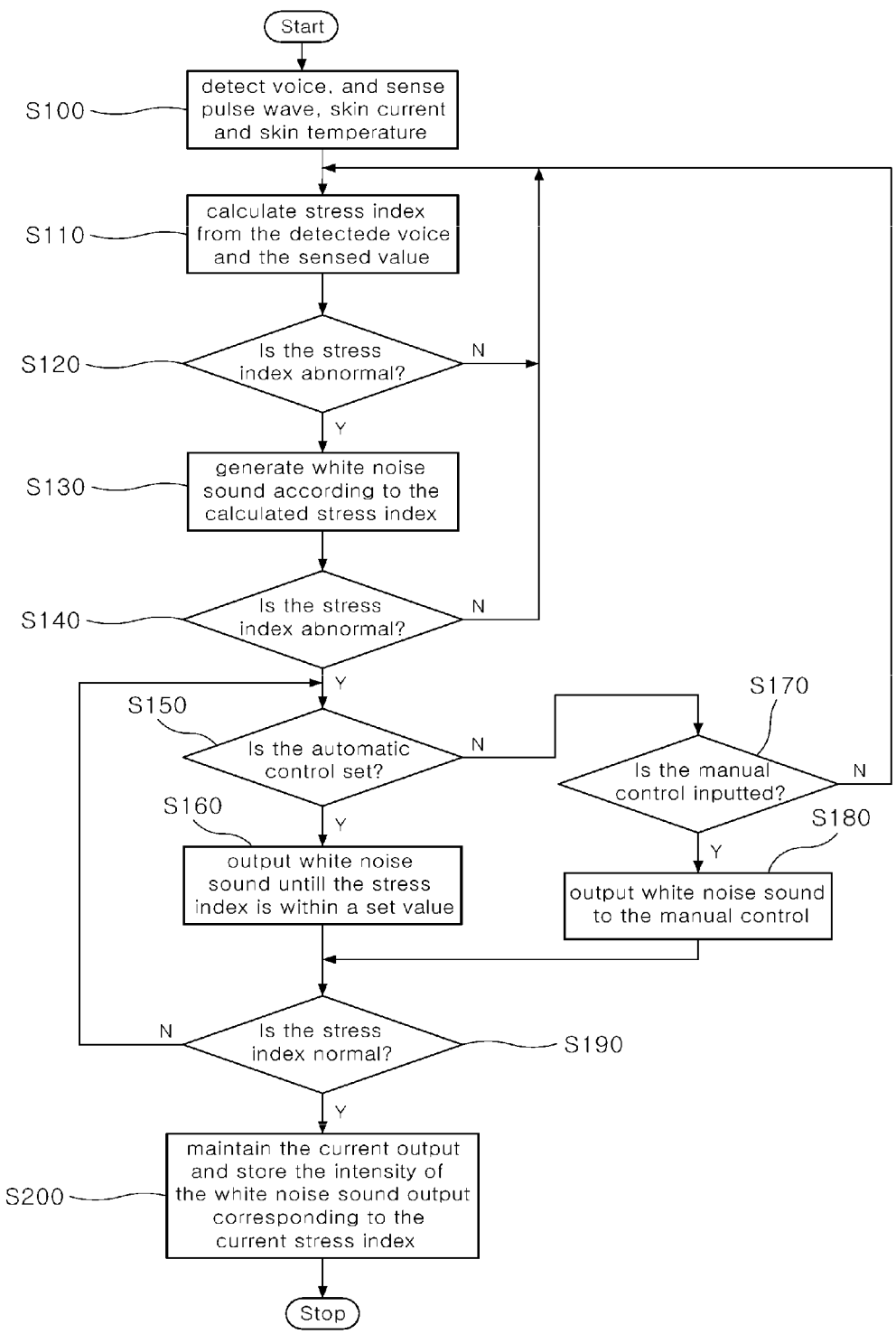
FIG. 4 is a flow chart showing a white noise generating method for stress relaxation and concentration improvement according to the present invention.

FIG. 4 is a flow chart showing a white noise generating method for stress relaxation and concentration improvement according to the present invention.

According to the present invention, as shown in FIG. 4, a white noise generating for stress relaxation and concentration improvement includes the step of: if a voice is detected from the microphone 11 of the headset 10 and one or more of the pulse wave, skin current and skin temperature are sensed from the sensor unit 13 at step S100, calculating by the voice stress calculating unit 22 a stress index from the detected voice and the sensed value in accordance with the stress index and physiological signal change at step S110.

After that, the control unit 27 determines whether the stress index is abnormal, that is, is greater or less than a threshold value as shown in FIG. 1 at step S120.

If it is determined that the stress index is abnormal at the step S120, the control unit 27 controls the white noise generating unit 23 so as to be generated the white noise with reference to the memory unit 24 in accordance with the calculated stress index, at step S130.

Next, the control unit 27 determines whether the stress index is abnormal or normal by means of the control unit 27 at step S140.

As a result, if the stress index is still abnormal at the step S140, it is determined whether automatic control is set or not at step S150.

If the automatic control is set at the step S150, the white noise sound is outputted again so that the stress index is within a pre-set value at step S160.

However, if the automatic control is not set at the step 150, it is determined whether manual control is inputted or not at step S170.

If the manual control is inputted at the step S170, the white noise sound is outputted by the manual control at step S180.

On the other hand, it is determined whether the stress index is normal or not by means of the control unit 27 at step S190.

If the control unit 27 determines whether the stress index is normal at the step S190, the current output is maintained and the intensity of the white noise sound output corresponding to the current stress index is stored in the memory unit 24 at step S200. Like this, the stored data is used to store in a table in which the intensities of the white noise sound outputs in accordance with the stress indexes calculated later are included.

The foregoing description of the embodiments of the invention has been presented for the purpose of illustration; it is not intended to be exhaustive or to limit the invention to the precise forms disclosed. Persons skilled in the relevant art can appreciate that many modifications and variations are possible in light of the above teachings. It is therefore intended that the scope of the invention be limited not by this detailed description, but rather by the claims appended hereto. The present invention may be modified in various ways and may have several exemplary embodiments. Specific exemplary embodiments of the present invention are illustrated in the drawings and described in detail in the detailed description. However, this does not limit the invention within specific embodiments and it should be understood that the invention covers all the modifications, equivalents, and replacements within the idea and technical scope of the invention. In the description, the portion of the components shown in the drawing may be magnified for the clarity and convenience of the description.

INDUSTRIAL APPLICABILITY

The present invention can be widely applied to a field of the white noise generating apparatus for stress relaxation and concentration improvement, so that the voice, pulse wave, skin current and skin temperature are measured by means of the headset to output the white noise capable of relieving stress or improving concentration.

What is claimed is:

1. A white noise generating apparatus for stress relaxation and concentration improvement, comprising:

a headset comprising a microphone configured to output a voice to a communication line, and a sound outputting unit configured to output the voice inputted from the communication line, and sensors configured to sense values of at least one item of a pulse wave, and a skin current of a wearer who wears the headset; and a white noise generator comprising a processor and configured to calculate a stress index from the voice outputted from the microphone to output white noise sound so that the stress index is within a normal range, the white noise generator further comprising a memory configured to store white noise data adequate to normalize stress in accordance with the stress index, an intensity of the white noise sound to be generated in accordance with the stress index, or the intensity of the white noise sound to be generated in accordance with a variation of a physiological signal of the at least one item of the pulse wave, and the skin current of the wearer, wherein the sensors include a photoplethsmography (PPG) sensor for sensing a pulse wave signal, which is measured from a finger or an ear by using a light emitting diode (LED) and a photodiode based on irradiation of LED light to a skin through the LED to vary vibration of pulses and measurement of an amount of light reflected to the photodiode, and a galvanic skin response (GSR) sensor for sensing the skin current, wherein the white noise generator extracts the voice outputted from the microphone, performs analysis of the extracted voice, compares the analyzed voice with pre-set voice information including a waveform, a period and an amplitude in accordance with a voice frequency, and calculates the stress index of the voice according to a set table, wherein the white noise generator is configured to calculate the stress index from the voice outputted from the microphone of the headset, and calculate sensed values based on at least one item of the pulse wave, and the skin current, sensed by the sensors, wherein the white noise generator is further configured to control to output the white noise sound to be within the normal range in accordance with the calculated stress index and the calculated sensed values, wherein, in response to determining that the stress index is abnormal, the white noise generator is further configured to generate and output the white noise through the headset so that the stress index becomes normal, wherein, in response to determining that an automatic control is not set, the processor of the white noise generator determines whether an input for a manual control is received, and wherein, in response to determining that the input for the manual control is received, the white noise generator is further configured to output the white noise sound by the manual control.

2. The white noise generating apparatus of claim 1, wherein the memory is connected to the processor, wherein the white noise generator is further configured to perform control to turn on/off a supply of operating power of the white noise generator.

3. A white noise generating method for stress relaxation and concentration improvement using a white noise generating apparatus, the white noise generating apparatus comprising a headset comprising a microphone, a sound outputting unit, and sensors configured to sense values of at least one item of a pulse wave, and a skin current of a wearer who wears the headset; and a white noise generator comprising a processor and configured to calculate a stress index from a voice outputted from the microphone to output white noise sound so that the stress index becomes within a normal range, the white noise generator further comprising a memory configured to store white noise data adequate to normalize stress in accordance with the stress index, an intensity of the white noise sound to be generated in accordance with the stress index, or the intensity of the white noise sound to be generated in accordance with a variation of a physiological signal of the at least one item of the pulse wave, and the skin current of the wearer, wherein the white noise generator is configured to calculate the stress index from the voice outputted from the microphone of the headset, and calculate sensed values of at least one item of the pulse wave, and the skin current sensed by the sensors, and wherein the white noise generator is further configured to control to output the white noise sound to be within the normal range in accordance with the calculated stress index and the calculated sensed values, the white noise generating method comprising:

extracting the voice outputted from the microphone, performing analysis of the extracted voice, comparing the analyzed voice with pre-set voice information including a waveform, a period and an amplitude in accordance with a voice frequency, and calculating the stress index of the voice according to a set table, detecting the voice outputted from the microphone of the headset and sensing values of at least one item of the pulse wave, and the skin current of the wearer who wears the headset wherein the sensors include a photoplethsmography (PPG) sensor for sensing a pulse wave signal, which is measured from a finger or an ear by using a light emitting diode (LED) and a photodiode based on irradiation of LED light to a skin through the LED to vary vibration of pulses and measurement of an amount of light reflected to the photodiode, and a galvanic skin response (GSR) sensor for sensing the skin current;

calculating, by the processor of the white noise generator, the stress index from the detected voice and the sensed value;

determining, by the processor of the white noise generator, whether or not the calculated stress index is abnormal;

in response to determining that the stress index is abnormal, generating and outputting the white noise through the headset so that the stress index becomes normal;

after generating and outputting of the white noise, by the processor of the white noise generator, determining whether or not the stress index is abnormal;

in response to determining that the stress index is still abnormal, determining whether an automatic control is set;

in response to determining that the automatic control is set, controlling and outputting the white noise sound again so that the stress index is within a pre-set value;

in response to determining that the automatic control is not set, determining whether an input for a manual control is received; and in response to determining that the input for the manual control is received, outputting the white noise sound by the manual control.

4. The white noise generating method of claim 3, further comprising, after controlling and outputting of the white noise sound so that the stress index becomes within the set value or outputting the white noise sound by the automatic control or the manual control:

determining whether the stress index is normal or not again; and in response to determining that the stress index is normal, maintaining the white noise sound that is currently outputted and storing an intensity of the white noise sound output corresponding to a current stress index in the memory.

* * * * *